US007163555B2

(12) United States Patent
Dinh

(10) Patent No.: US 7,163,555 B2
(45) Date of Patent: Jan. 16, 2007

(54) DRUG-ELUTING STENT FOR CONTROLLED DRUG DELIVERY

(75) Inventor: Thomas Q. Dinh, Minnetonka, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 217 days.

(21) Appl. No.: 10/408,920

(22) Filed: Apr. 8, 2003

(65) Prior Publication Data

US 2004/0204750 A1   Oct. 14, 2004

(51) Int. Cl.
*A61F 2/06* (2006.01)
(52) U.S. Cl. .................................... 623/1.42; 623/1.18
(58) Field of Classification Search ............... 623/1.42, 623/1.15, 1.18, 1.43
See application file for complete search history.

(56) References Cited

U.S. PATENT DOCUMENTS

| 5,769,884 A * | 6/1998 | Solovay ..................... 623/1.13 |
| 5,843,172 A | 12/1998 | Yan |
| 5,891,108 A | 4/1999 | Leone et al. |
| 6,071,305 A | 6/2000 | Brown et al. |
| 6,214,901 B1 | 4/2001 | Chudzik et al. |
| 6,273,913 B1 | 8/2001 | Wright et al. |
| 6,758,859 B1 * | 7/2004 | Dang et al. ................. 623/1.15 |
| 2001/0027340 A1 | 10/2001 | Wright et al. |
| 2002/0082680 A1 * | 6/2002 | Shanley et al. ............. 623/1.16 |

FOREIGN PATENT DOCUMENTS

| EP | 950386 A2 * | 10/1999 |
| EP | 1466634 | 10/2004 |
| WO | WO 2002/32347 | 4/2002 |
| WO | WO 2002/43619 | 6/2002 |

* cited by examiner

*Primary Examiner*—Eduardo C. Robert
*Assistant Examiner*—Thomas J. Sweet

(57) ABSTRACT

The present invention provides a stent for delivering drugs to a vessel in a body, including a stent framework with a plurality of reservoirs formed therein, a drug polymer positioned in the reservoirs, and a polymer layer positioned on the drug polymer. The present invention also provides a method of manufacturing a drug-polymer stent and a method of treating a vascular condition using the drug-polymer stent.

23 Claims, 14 Drawing Sheets

600

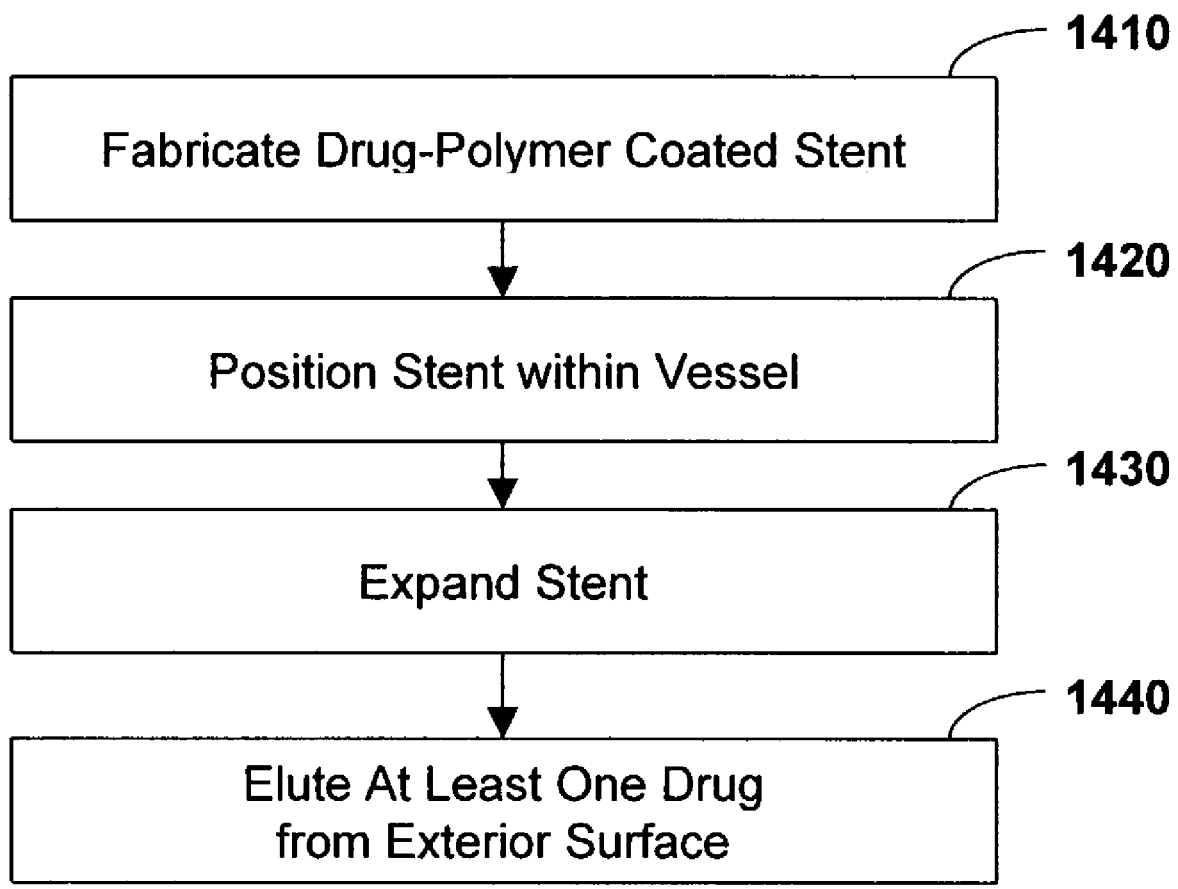

DRUG-ELUTING STENT FOR CONTROLLED DRUG DELIVERY

FIELD OF THE INVENTION

This invention relates generally to biomedical stents. More specifically, the invention relates to an endovascular stent with bioactive drugs for in vivo, timed-release drug delivery.

BACKGROUND OF THE INVENTION

Drug-coated stents can improve the overall effectiveness of angioplasty and stenotic procedures performed on the cardiovascular system and other vessels within the body by delivering potent therapeutic compounds at the point of infarction. Drugs such as anti-inflammatants and anti-thrombogenics may be dispersed within the drug-polymer coating and released gradually after insertion and deployment of the stent. These drugs and coatings can reduce the trauma to the local tissue bed, aid in the healing process, and significantly reduce the narrowing or constriction of the blood vessel that can reoccur where the stent is placed.

The conventional approach to drug-coated stents incorporates the therapeutic agent into a polymeric solution and then coats the stent, such as described in "Bioactive Agent Release Coating" by Chudzik et al., U.S. Pat. No. 6,214,901, issued Apr. 10, 2001. The ideal coating must be able to adhere strongly to the metal stent framework both before and after expansion of the stent, and be able to control release the drug at sufficient therapeutic levels for several days, weeks or longer. Unfortunately, some drug polymers do not provide the mechanical flexibility necessary to be effectively used on a stent. A stent may be deployed by self-expansion or balloon expansion, accompanied by a high level of bending at portions of the stent framework, which can cause cracking, flaking, peeling, or delaminating of many candidate drug polymers while the stent diameter is increased by threefold or more during expansion. The coating must also be thin enough as not to significantly increase the profile of the stent. These types of coated stents allow drugs to diffuse to the vessel walls as well as into the blood stream through the lumen. Bioactive agents diffused into the vessel wall increase efficacy and patent pharmaceutical effects at the point of need, whereas drugs diffused into the blood stream may be quickly flushed away and become ineffective, thereby requiring thicker coatings or a greater amount of drugs to be loaded into the stent coating.

A possible alternative to a coated stent is a stent containing reservoirs that are loaded with a drug, as discussed by Wright et al., in "Modified Stent Useful for Delivery of Drugs Along Stent Strut," U.S. Pat. No. 6,273,913, issued Aug. 14, 2001; and Wright et al., in "Stent with Therapeutically Active Dosage of Rapamycin Coated Thereon," US patent publication US 2001/0027340, published Oct. 4, 2001. This type of system seems to work well if there is only one drug to load and if the reservoirs are small. However, when the reservoirs are large such as with long channels, repeated loadings of a drug by dipping would pose some challenging problems due to excessive build-up of a drug polymer on the stent framework.

Wright et al. in U.S. Pat. No. 6,273,913, describes the delivery of rapamyacin from an intravascular stent and directly from micropores formed in the stent body to inhibit neointinal tissue proliferation and restenosis. The stent, which has been modified to contain micropores, is dipped into a solution of rapamycin and an organic solvent, and the solution is allowed to permeate into the micropores. After the solvent has been allowed to dry, a polymer layer may be applied as an outer layer for a controlled release of the drug.

U.S. Pat. No. 5,843,172 by Yan, which is entitled "Porous Medicated Stent", discloses a metallic stent that has a plurality of pores in the metal that are loaded with medication. The drug loaded into the pores is a first medication, and an outer layer or coating may contain a second medication. The porous cavities of the stent can be formed by sintering the stent material from metallic particles, filaments, fibers, wires or other materials such as sheets of sintered materials.

Leone et al. in U.S. Pat. No. 5,891,108 entitled "Drug Delivery Stent" describes a retrievable drug delivery stent, which is made of a hollow tubular wire. The tubular wire or tubing has holes in its body for delivering a liquid solution or drug to a stenotic lesion. Brown et al. in "Directional Drug Delivery Stent and Method of Use," U.S. Pat. No. 6,071,305 issued Jun. 6, 2000, discloses a tube with an eccentric inner diameter and holes or channels along the periphery that house drugs and can deliver them preferentially to one side of the tube. Scheerder et al. in US patent publication US 2002/0007209, discloses a series of holes or perforations cut into the struts on a stent that are able to house therapeutic agents for local delivery.

It is desirable to have a medicated stent that can be tailored to provide a desired elution rate for one or more drugs and to provide sufficient quantities of bioactive agents without compromising the mechanics of the stent during deployment and use. It would be beneficial to have a drug-polymer system that can be tailored to accommodate a variety of drugs for controlled time delivery, while maintaining mechanical integrity during stent deployment. Furthermore, it would be beneficial to provide a drug-polymer stent with phased delivery of drugs in effective quantities.

It is an object of this invention, therefore, to provide a framework and structure for effective, controlled delivery of suitable quantities of pharmaceutical agents from medicated stents. It is a further object to provide a system and method for treating heart disease and other vascular conditions, to provide methods of manufacturing drug-polymer stents, and to overcome the deficiencies and limitations described above.

SUMMARY OF THE INVENTION

One aspect of the present invention provides a stent for delivering drugs to a vessel in a body comprising a stent framework including a plurality of reservoirs, a drug-polymer layer positioned in the reservoirs, and a polymer layer positioned on the drug polymer.

The stent may include a cap layer disposed on the interior surface of the stent framework, the cap layer covering at least a portion of the through-holes and providing a barrier characteristic to inhibit the elution of a drug in the drug polymer from the interior surface of the stent framework.

A method of manufacturing a drug-polymer stent and a method of treating a vascular condition using the drug-polymer stent are also disclosed herein.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present inven-

BRIEF DESCRIPTION OF THE DRAWINGS

Various embodiments of the present invention are illustrated by the accompanying figures, wherein:

FIG. 14 is a flow diagram of a method for treating a vascular condition, in accordance with one embodiment of the current invention.

DETAILED DESCRIPTION OF THE PRESENTLY PREFERRED EMBODIMENTS

Figure 1:
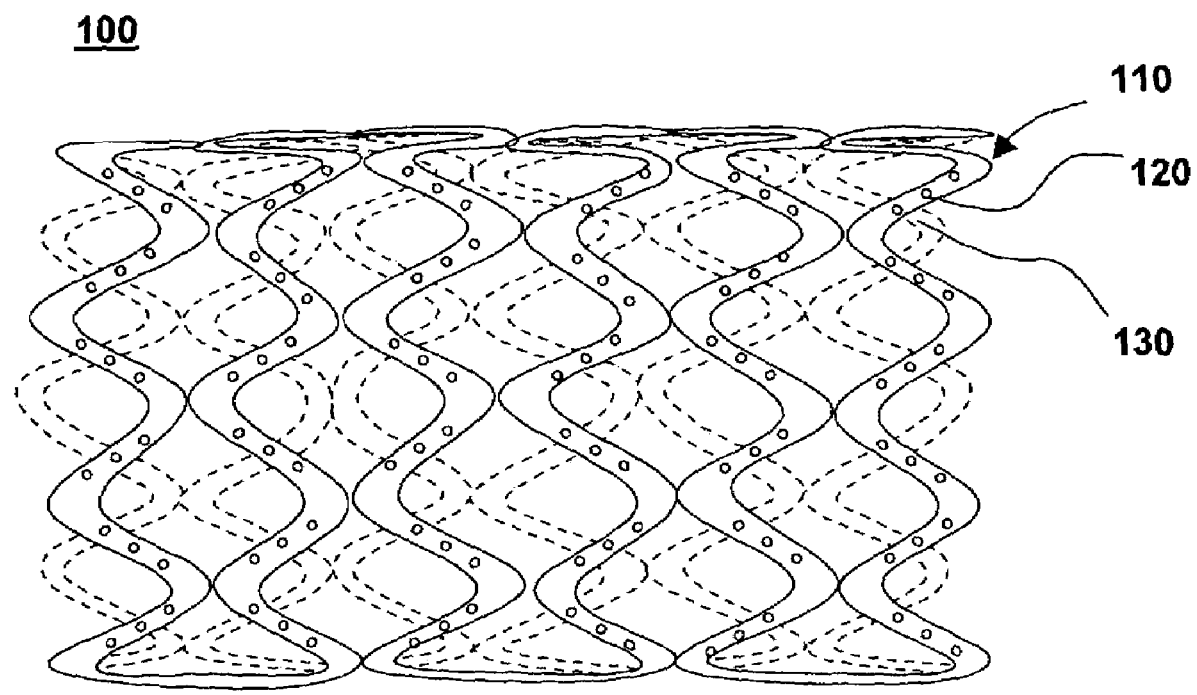
FIG. 1 is an illustration of a stent for delivering drugs to a vessel in a body, in accordance with one embodiment of the current invention.

FIG. 1 shows one embodiment of a stent for delivering drugs to a vessel in a body, in accordance with the present invention. Drug-polymer stent 100 comprises a stent framework 110 with a plurality of reservoirs 120 formed therein, and a drug polymer 130 with a polymer layer positioned on the drug polymer. Drug polymer 130 with the polymer layer comprises at least one therapeutic compound.

Various drugs are loaded into reservoirs 120 on stent framework 110 that face the arterial wall. Different types of drug polymers 130 and polymer layers are positioned in reservoirs 120 for release of drugs at various stages of restenosis. In one embodiment, drug-polymer stent 100 comprises a plurality of reservoirs where drugs are deposited in layers. Optionally, polymer membranes may be positioned in between the drug-polymer layers for controlled release of various drugs. Drugs such as anti-proliferatives, anti-inflammatants, anti-thrombotic drugs, antisense drugs, gene therapies and therapeutic peptides can be loaded on the stent for delivery during the different stages of the restenotic process. The drugs in the form of drug polymers may be deposited in layers with polymer membranes in between for controlled release. Drugs in the form of microspheres, powders, and other forms may also be positioned in the reservoirs. Applications of the drug-polymer stent include restenotic treatments of coronary blood vessels after balloon angioplasty and stenting, treatment of instent hyperplasia, and local drug delivery to blood vessel walls.

Stent framework 110 is typically cylindrically oriented such that an exterior surface of the stent framework contacts the vessel wall when deployed in the body, and an interior surface of the stent framework is in contact with the blood or other bodily fluids flowing through the vessel. Stent framework 110 may comprise a metallic base or a polymeric base. The metallic base may comprise a material such as stainless steel, nitinol, tantalum, MP35N alloy, platinum, titanium, a suitable biocompatible alloy, or any combination thereof. Stent framework 110 may comprise any suitable biocompatible polymer.

Reservoirs 120 are formed on the exterior surface of stent framework 110. Reservoirs 120 may contain drugs, drug polymers, adhesive layers, barrier layers and cap layers. Reservoirs 120 are formed of suitable sizes, shapes, quantities and locations to house the drugs and to deliver the drugs at preferred rates and quantities in the directions of interest. For example, reservoirs 120 may comprise a plurality of through-holes or channels formed in stent framework 110. Reservoirs 120 are suitably large so that they are readily formed and can contain ample amount of drugs. Reservoirs 120 are shaped such that large amounts of drugs can be contained therein without unduly affecting the mechanical integrity of the stent framework. Reservoirs 120 are positioned along the stent struts at spacings that allow relatively uniform drug delivery to the vessel wall. Reservoirs 120 are positioned such that the channels or openings are directed outwardly in a direction of preferred drug delivery. Reservoirs 120 may have openings on the interior surface of stent framework 110 so that a certain portion of the drug may be delivered to the fluid flowing through the vessel or to tissue buildup around the stent framework. Drug polymers positioned within reservoirs 120 are less prone to cracking and flaking than coatings disposed on stent framework 110 when the stent is deployed.

Drug polymer 130 with a polymer layer positioned thereon comprises one or more pharmaceutical compounds. The polymer layer may comprise a barrier layer, a cap layer, or another drug polymer. Drug polymer 130 is positioned in one or more reservoirs 120 on stent framework 110. The barrier layer or cap layer may cover a portion or the entire stent framework in addition to drug polymer 130. Although drugs can be effectively dispersed within a drug-polymer coating disposed on the stent framework, an advantage of the reservoir approach is that drug polymers within the reservoirs are less subject to flaking and peeling when the stent is expanded.

Another aspect of the invention is a stent with a plurality of reservoirs for combinations of synergistic drugs. Drugs with synergistic actions are deposited in the channels at the same time and a polymeric barrier layer is used for a controlled release of the drugs to the arterial wall.

The polymeric barrier layer also can be used for the delivery of drugs. For example, an antithrombotic drug such as hirudin or heparin can be incorporated into the outer polymer membrane for the prevention of acute thrombosis.

Figure 2:
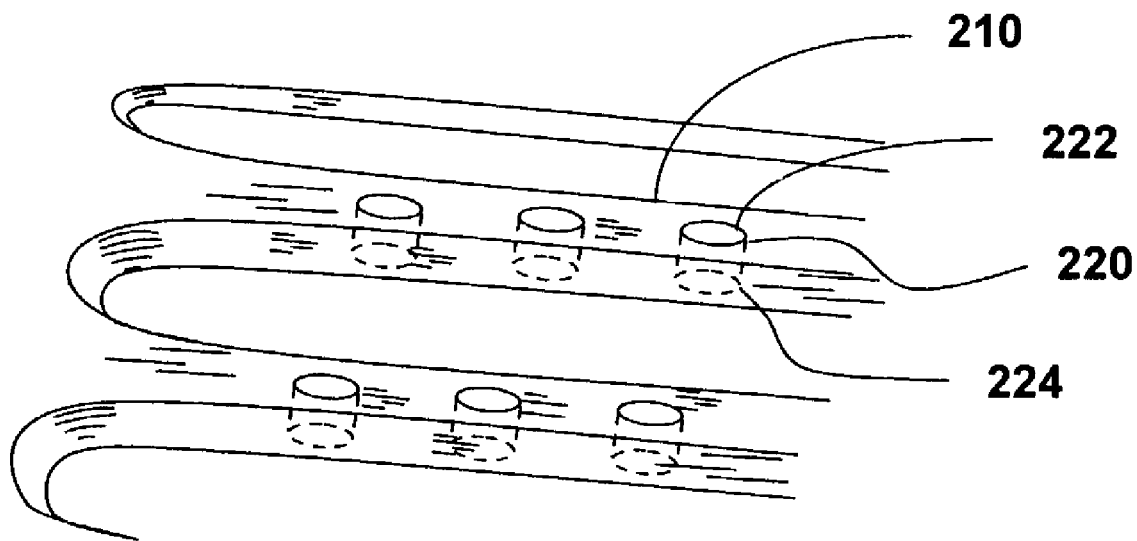
FIG. 2 is a perspective view of a portion of a drug-polymer stent framework with through-holes, in accordance with one embodiment of the current invention.

FIG. 2 shows a perspective view of a portion of a drug-polymer stent framework with through-holes, in, accordance with one embodiment of the present invention at 200. Drug-polymer stent framework 200 comprises a stent framework 210 with a plurality of reservoirs 220 formed therein. Reservoirs 220 comprise a plurality of through-holes. The through-holes illustrated here have a first open region 222 on an exterior surface of stent framework 210 and a second open region 224 on an interior surface of stent framework 210, with a nominally uniform diameter throughout each through-hole. Reservoirs 220 are sized and positioned such that suitable quantities of drugs can be delivered to places of interest along the vessel wall. The through holes may have a diameter up to roughly half the width of the stent framework.

Figure 3:
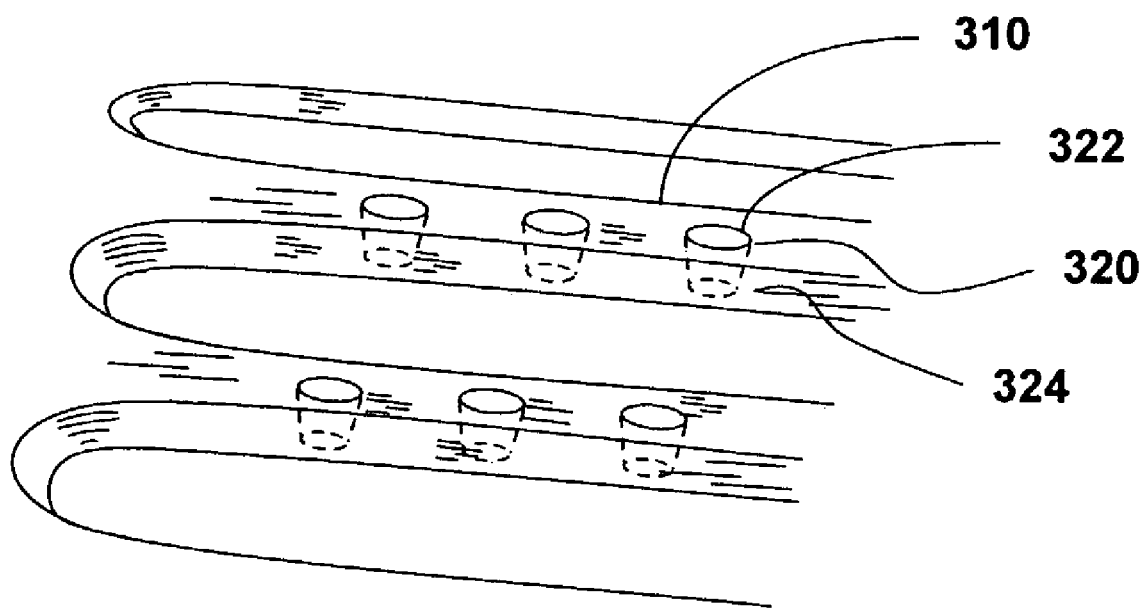
FIG. 3 is a perspective view of a portion of a drug-polymer stent framework with tapered through-holes, in accordance with one embodiment of the current invention.

FIG. 3 shows a perspective view of a portion of a drug-polymer stent framework with tapered through-holes, in accordance with one embodiment of the present invention at 300. Drug-polymer stent framework 300 comprises a stent framework 310 with a plurality of reservoirs 320 formed therein. Reservoirs 320 comprise a plurality of tapered through-holes. The tapered through-holes have a first open region 322 on an exterior surface of stent framework 310 and a second open region 324 on an interior surface of stent framework 310, the tapered through-holes having a larger diameter at the exterior surface of stent framework 310, a smaller diameter at the interior surface of stent framework 310, and a relatively uniform taper connecting open region 322 and open region 324. Reservoirs 320 are sized and positioned such that suitable quantities of drugs can be delivered to places of interest along the vessel wall. Tapered through-holes allow more drugs to be delivered to the exterior surface than the interior surface, since the exposed area for drug elution is larger at the exterior surface of stent framework 310. The taper may be linear or curved, the curved taper allowing more drugs to be positioned in stent framework 310.

Figure 4:
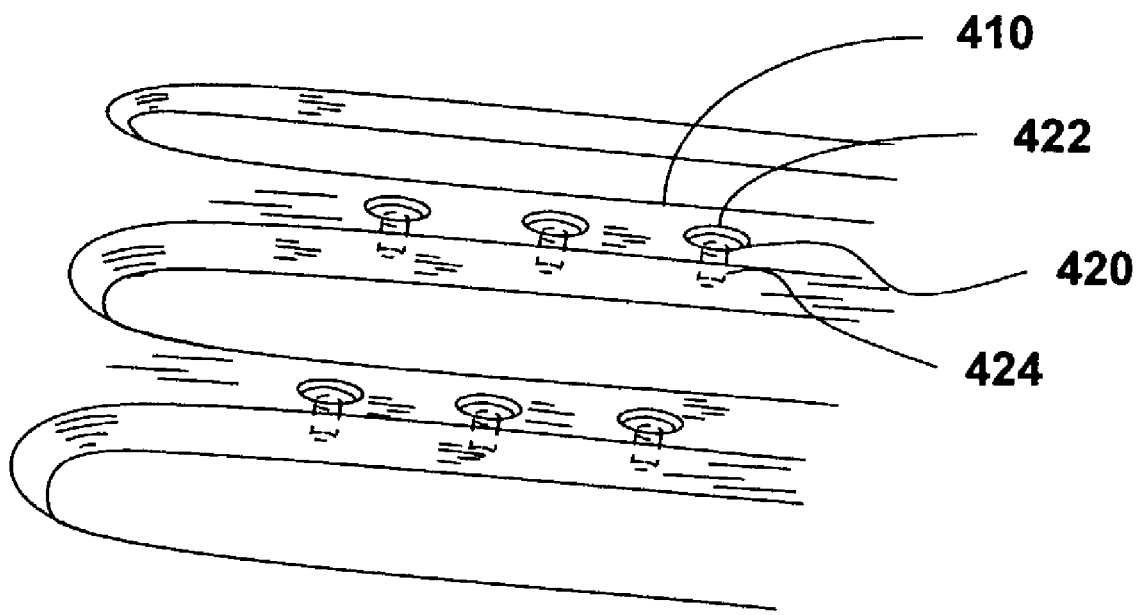
FIG. 4 is a perspective view of a portion of a drug-polymer stent framework with staged through-holes, in accordance with one embodiment of the current invention.

FIG. 4 shows a perspective view of a portion of a drug-polymer stent framework with staged through-holes, in accordance with one embodiment of the present invention at 400. Drug-polymer stent framework 400 comprises a stent framework 410 with a plurality of reservoirs 420 formed therein. Reservoirs 420 comprise a plurality of staged through-holes. The staged through-holes have a first open region 422 on an exterior surface of stent framework 410 and a second open region 424 on an interior surface of stent framework 410. First open region 422 has a first diameter and second open region 424 has a second diameter, the first diameter being larger than the second diameter. The staged through-holes are sized and positioned so that suitable quantities of drugs can be delivered along the vessel wall once the stent is deployed. The staged through-holes are typically concentric, and can comprise one or more steps or shoulders within the through-hole. Upper portions of the staged through-holes may overlap.

Figure 5:
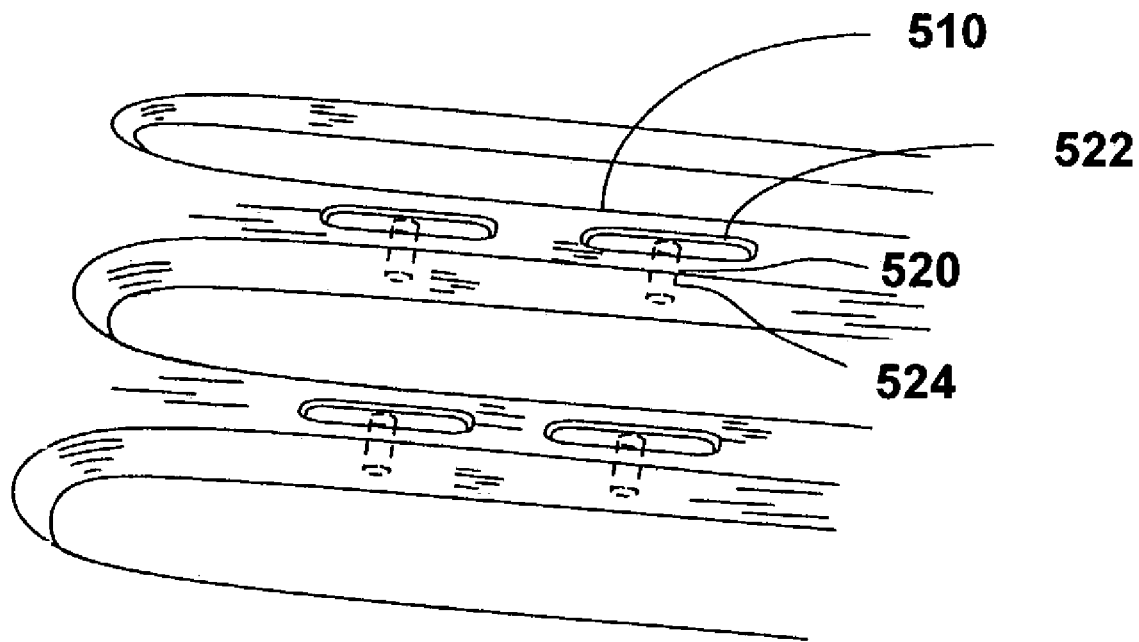
FIG. 5 is a perspective view of a portion of a drug-polymer stent framework with through-holes and channels along an exterior surface of the stent, in accordance with one embodiment of the current invention.

FIG. 5 shows a perspective view of a portion of a drug-polymer stent framework with through-holes and channels along an exterior surface of the stent, in accordance with one embodiment of the present invention at 500. Drug-polymer stent framework 500 comprises a stent framework 510 with a plurality of reservoirs 520 formed therein. Reservoirs 520 comprise a plurality of through-holes combined with channels. The through-holes with channels have a first open region 522 on an exterior surface of stent framework 510 and a second open region 524 on an interior surface of stent framework 510. First open region 522 has an elongated opening on the exterior surface of the stent framework, and second open region 524 has a smaller, nominally circular region on the interior surface. The through-holes with channels are sized and positioned along the stent framework so that suitable quantities of drugs can be delivered along the vessel wall. The channels may separated from each other or partially overlap.

Figure 6:
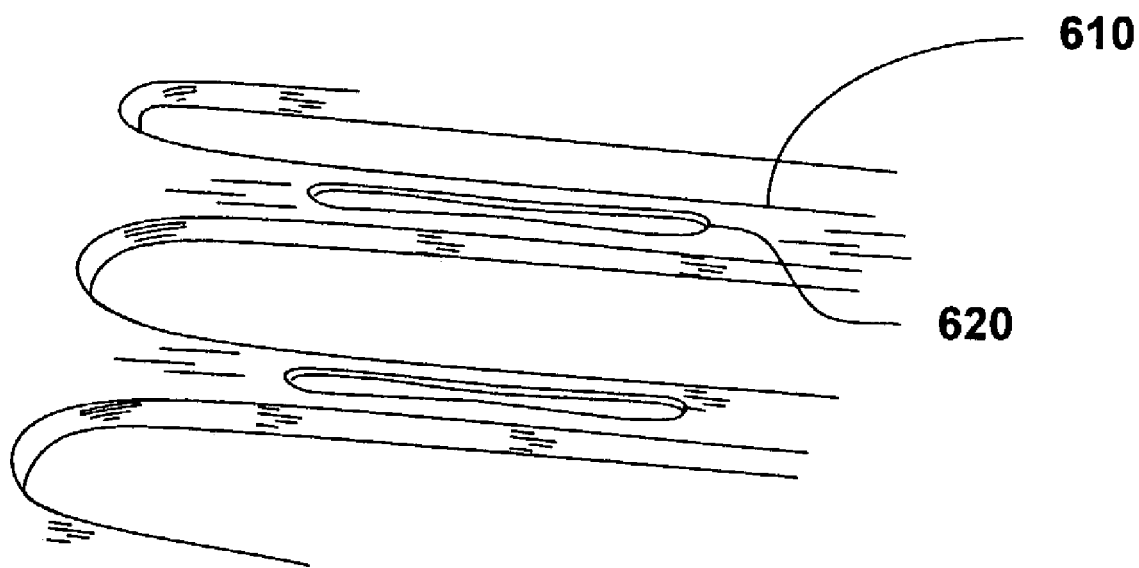
FIG. 6 is a perspective view of a portion of a drug-polymer stent framework with channels on an exterior surface of the stent, in accordance with one embodiment of the current invention.

FIG. 6 shows a perspective view of a portion of a drug-polymer stent framework with channels on an exterior surface of the stent, in accordance with one embodiment of the present invention at 600. Drug-polymer stent framework 600 comprises a stent framework 610 with a plurality of reservoirs 620 formed therein. Reservoirs 620 comprise a plurality of channels along the exterior surface of stent framework 610. The channels are typically long regions with parallel sides, boxed ends with curved corners, and a bottom comprised of the base material of stent framework 610. Channel reservoirs 620 are sized and positioned along the stent framework so that suitable quantities of drugs can be delivered along the vessel wall as desired. The channels may be on the order of 30 to 60 microns wide, limited generally by the width of the stent framework. The channels may be on the order of 10 to 50 microns deep, typically limited to about one-half of the thickness of the stent framework. The channels may be up to 1 millimeter in length or longer. In one embodiment, the channel reservoirs may be formed by saw cuts across the stent framework, along the stent framework, or at an angle to the stent framework.

Figure 7:
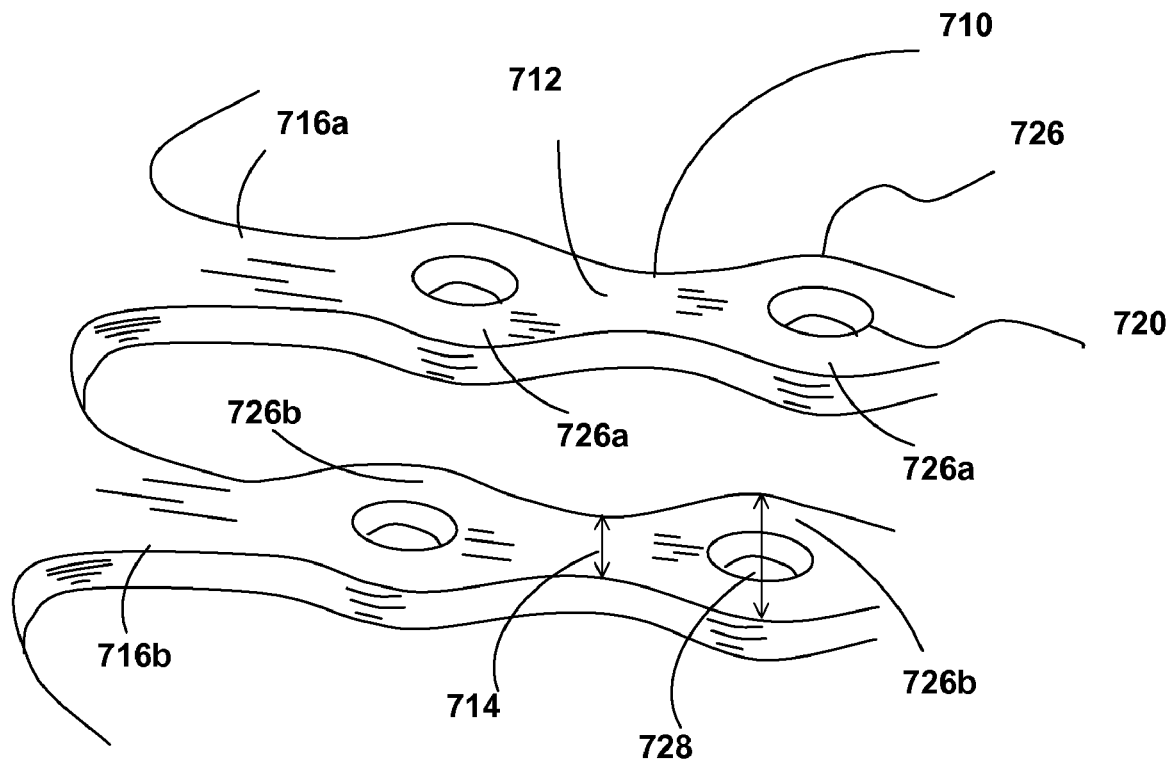
FIG. 7 is a perspective view of a portion of a drug-polymer stent framework with enlargements in the vicinity of the through-holes, in accordance with one embodiment of the current invention.

FIG. 7 shows a perspective view of a portion of a drug-polymer stent framework with enlargements in the vicinity of the through-holes, in accordance with one embodiment of the current invention at 700. Drug-polymer stent framework 700 comprises a stent framework 710 having a plurality of struts 716. FIG. 7 illustrates portions of two adjacent struts 716a and 716b. Each of the struts 716 includes a plurality of reservoirs 720 formed therein. Reservoirs 720 are illustrated with straight-walled through-holes in this example. An enlarged region 726 is formed in the vicinity of the through-hole to reduce stress when the stent is expanded. Stent framework 710 further includes narrow regions 712. Narrow regions 712 are positioned in an alternating pattern with enlarged regions (enlargements) 726 so that a narrow region 712 is on both sides of each enlarged region 726. Enlarged regions 726 have a first width 728 greater than a second width 714 of narrow regions 712. The enlarged regions 726 of each strut 716 align with the enlarged regions of each adjacent strut 716. As illustrated in FIG. 7, enlarged regions 726a of strut 716a align with enlarged regions 726b of strut 716b when the stent is in at least a compressed (i.e. unexpanded or crimped) configuration. As the stent is expanded, bending stresses result in the base material of the stent framework. These stresses are typically enhanced in the region of a hole, though they can be mitigated by additional material around the hole. The enlargements are readily formed, for example, when high-powered lasers are used to cut the stent framework from a thin-walled tube of base material.

Figure 8:
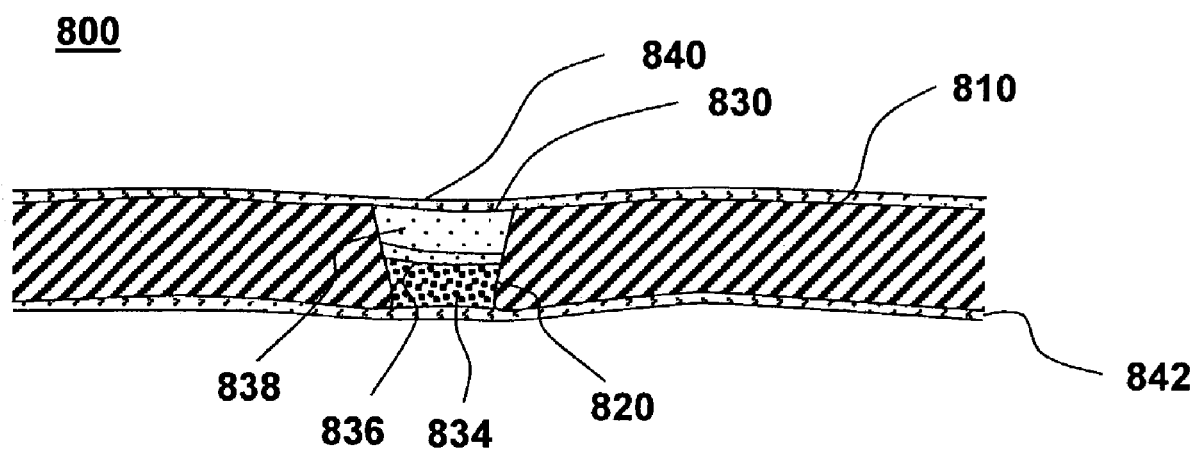
FIG. 8 is a cutaway view of a portion of a drug-polymer stent framework with drug polymers positioned in tapered through-holes, in accordance with one embodiment of the current invention.

FIG. 8 shows a cutaway view of a portion of a drug-polymer stent framework with drug polymers positioned in a tapered through-hole, in accordance with one embodiment of the present invention at 800. Drug-polymer stent framework 800 comprises a stent framework 810 with a reservoir 820, and a drug polymer 830 with a polymer layer positioned in reservoir 820. Stent framework 810 comprises a metallic or polymeric base. Reservoir 820 is illustrated in this example with a tapered through-hole. The polymer layer may be a barrier layer, a cap layer, or another drug polymer.

In one embodiment, drug polymer 830 with a polymer layer may comprise a first layer 834 of a first drug polymer having a first pharmaceutical characteristic and a second layer 838 of a second drug polymer having a second pharmaceutical characteristic. The polymer layer may comprise a drug polymer. Alternatively, drug polymer 830 with a polymer layer may comprise several drug polymer layers in addition to a polymer layer, the polymer layer serving as a cap layer or a barrier layer, yet having no pharmaceutical compounds.

Drug polymers of first layer 834 and second layer 838 comprise at least one therapeutic compound. The therapeutic compounds include an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, or a combination thereof.

In another embodiment, drug polymer 830 with a polymer layer may comprise a first drug-polymer layer including an anti-proliferative drug, a second drug-polymer layer including an anti-inflammatory drug, and a third drug-polymer layer including an antisense drug. The antisense drug, the anti-inflammatory drug and the anti-proliferative drug are eluted in a phased manner when the stent is deployed.

A barrier layer 836 may be positioned between drug polymer 830 and the polymer layer. A barrier layer 836 may be positioned between first layer 834 and second layer 838. Barrier layer 836 provides a barrier characteristic that controls the elution of drug from first layer 834 into the walls of the vessel where the stent is deployed. The barrier layer comprises a relatively thin polymeric material. Examples of the polymeric materials suitable for use as a barrier layer include a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, or a combination thereof.

Drug polymer 830 with polymer layer may comprise a drug polymer with a pharmaceutical compound and a cap layer positioned on the drug polymer. Cap layer 840 may be positioned over drug polymer 830. Cap layer 840 may also be disposed on at least a portion of an interior surface or an exterior surface of stent framework 810. Cap layer 840 provides a barrier characteristic to control the elution of drugs from drug polymer 830 with a polymer layer. Cap layer 840 may comprise a polymer such as, for example, a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, or a combination thereof.

A cap layer 842 may be positioned on an interior surface of stent framework 810. Cap layer 842 may be disposed on the interior surface of the stent framework, covering at least a portion of the through-holes and providing a barrier characteristic to control the elution rate of one or more drugs in drug polymer 830 from the interior surface of stent framework 810. Cap layer 842 may also cover at least a portion of the interior surface of stent framework 810. Cap layer 842, for example, may inhibit the elution of any drugs in drug polymer 830 from the interior surface of stent framework 810. Cap layer 842, for example, may inhibit the elution of one type of drug and pass another type of drug for delivery to the interior of the vessel where the stent is deployed. Cap layer 842 may comprise a suitable polymer layer such as, for example, a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, or a combination thereof. Optionally, an adhesion layer may be positioned between the stent framework and the drug polymer.

Figure 9:
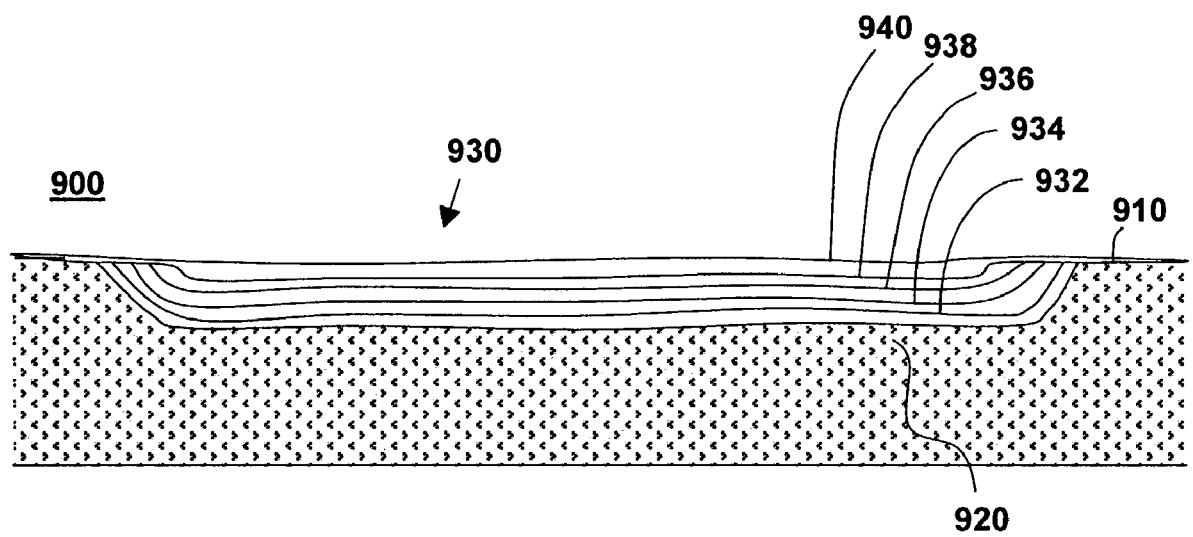
FIG. 9 is a cutaway view of a portion of a drug-polymer stent framework with drug polymers positioned in channels, in accordance with one embodiment of the current invention.

FIG. 9 shows a cutaway view of a portion of a drug-polymer stent framework with drug polymers positioned in channels, in accordance with one embodiment of the present invention at 900. Drug-polymer stent framework 900 comprises a stent framework 910, a plurality of reservoirs 920, and a drug polymer 930 with a polymer layer. The polymer layer may comprise a cap layer, a barrier layer, or another drug polymer. Additional cap layers, barrier layers and drug polymer layers may be included. Reservoir 920 is illustrated in this example as a plurality of channels on an exterior surface of stent framework 910.

Drug polymer 930 with a polymer layer, in one example, comprises a first layer 934 of a drug polymer and a second layer 938 of a second drug polymer that may be different than the first. Optionally, a third layer of a third drug polymer may be added to provide a phased delivery of drugs to the vessel in which the stent is deployed. A barrier layer 936 may be positioned between first layer 934 and second layer 938. A second barrier layer may be positioned between second layer 938 and a third drug-polymer layer. The barrier layers provide a barrier characteristic to control the elution rate of drugs from the medicated stent.

An adhesion layer 932 may be disposed between first layer 934 of a drug polymer and stent framework 910. Adhesion layer 932 may enhance the adhesion between a metallic surface such as the base or walls of the reservoirs and the drug polymers. Examples of adhesion coatings include a polyurethane, a phenoxy, poly(lactide-co-glycolide), polylactide, polysulfone, polycaprolactone, an adhesion promoter, or combinations thereof.

Cap layer 940 may be positioned on the drug polymers and may cover a portion of the surface of stent framework 910. Examples of cap layer materials include a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, or combinations thereof. A continuation of cap layer 940 or a second cap layer may be placed on the interior surface of stent framework 910.

Figure 10:
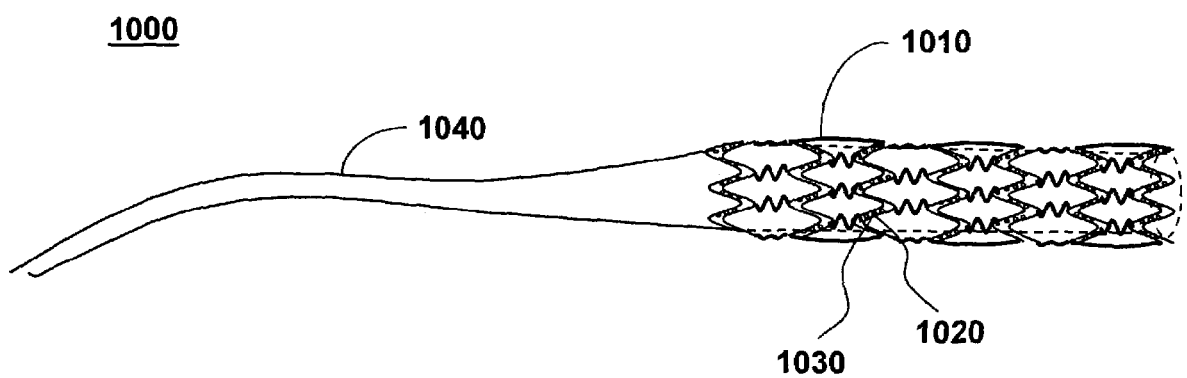
FIG. 10 is an illustration of a system for treating a vascular condition including a catheter and a drug-polymer stent, in accordance with one embodiment of the current invention.

FIG. 10 shows an illustration of a system for treating a vascular condition including a catheter and a drug-polymer stent, in accordance with one embodiment of the present invention at 1000. One aspect of the present invention is a system for treating heart disease, various cardiovascular ailments, and other vascular conditions using catheter-deployed endovascular stents with reservoirs, drug polymers positioned in the reservoirs, and polymer layers for controlling the release and phasing of bioactive agents and drugs from the reservoirs. Treating vascular conditions refers to the prevention or correction of various ailments and deficiencies associated with the cardiovascular system, urinogenital systems, biliary conduits, abdominal passageways and other biological vessels within the body using stenting procedures.

In this embodiment, vascular condition treatment system 1000 includes a stent framework 1010, a plurality of reservoirs 1020 formed in the stent framework, a drug polymer 1030 with a polymer layer, and a catheter 1040 coupled to stent framework 1010. Catheter 1040 may include a balloon used to expand the stent, or a sheath that retracts to allow expansion of the stent. Drug polymer 1030 includes one or more bioactive agents. The bioactive agent is a pharmacologically active drug or bioactive compound. The polymer layer comprises a barrier layer, a cap layer, or another drug polymer. The polymer layer provides a controlled drug-elution characteristic for each bioactive agent or drug. Drug elution refers to the transfer of the bioactive agent out from drug polymer 1030. The elution is determined as the total amount of bioactive agent excreted out of the drug polymer, typically measured in units of weight such as micrograms, or in weight per peripheral area of the stent. In one embodiment, the drug polymer includes between 0.5 percent and 50 percent of the bioactive agent of drug by weight.

Upon insertion of catheter 1040 and stent framework 1010 with drug polymer into a directed vascular region of a human body, stent framework 1010 may be expanded by applying pressure to a suitable balloon inside the stent, or by retracting a sheath to allow expansion of a self-expanding stent. Balloon deployment of stents and self-expanding stents are well known in the art. Catheter 1040 may include the balloon used to expand stent framework 1010. Catheter 1040 may include a sheath that retracts to allow expansion of a self-expanding stent.

Figure 11:
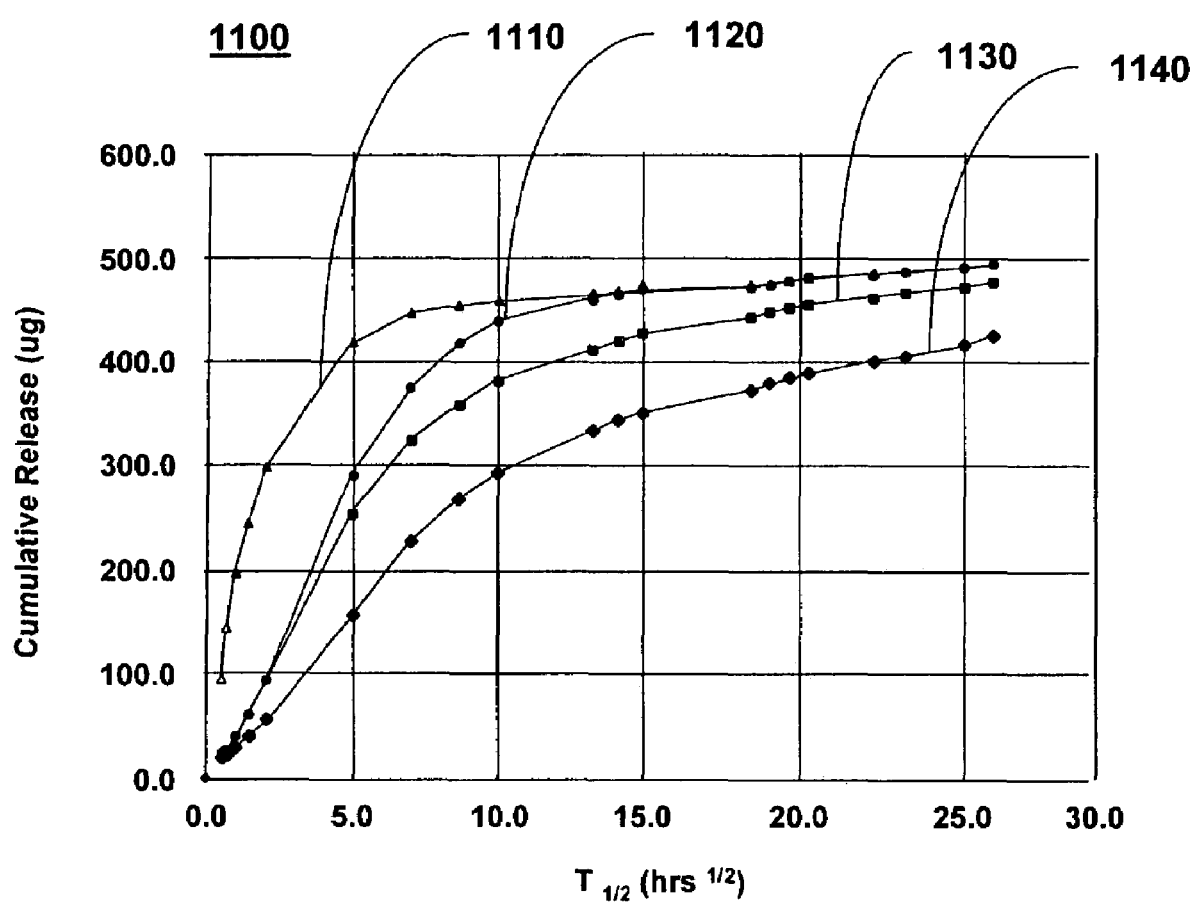
FIG. 11 is a plot of cumulative release of a drug from a drug-polymer stent, in accordance with one embodiment of the current invention.

FIG. 11 shows a plot of cumulative release of a drug from a drug-polymer stent, in accordance with one embodiment of the present invention at 1100. Cumulative release plot 1100 shows the release kinetics of an antisense compound from channel stents with various cap-coating polymers. The chart shows the cumulative release of drug in micrograms over a 700-hour period in a phosphate-buffered saline (PBS) solution at 37 degrees centigrade, with time plotted on a square-root scale. UV-Vis spectrophotometry is used to determine the amount of drug released. An aliquot of the PBS solution is removed at prescribed intervals and used for the analysis. In curve 1110, a cap layer of polycaprolactone (PCL) is used on two samples, and the average elution of the antirestenotic drug is shown to initially have the highest elution rate. In curve 1120, a cap layer of PurSil™ 20–80A, a silicone-urethane copolymer, is dissolved in a solution of tetrahydrofuran (THF) or chloroform with 4% methoxy-poly(ethylene glycol) (mPEG) to modify the end groups of the silicone-urethane copolymer. The drug polymer is applied to reservoirs and covered with the cap layer. The stent is monitored for drug release, with an initial rate appreciably less than curve 1110, though with a higher rate than curve 1110 at later times. In curve 1130, a cap layer of PurSil™ 20–80A is unmodified and shows a similar initial rate to curve 1120. In curve 1140, PurSil™ 20–80A modified with 2% sme is shown to have even a slower elution rate.

Figure 12:
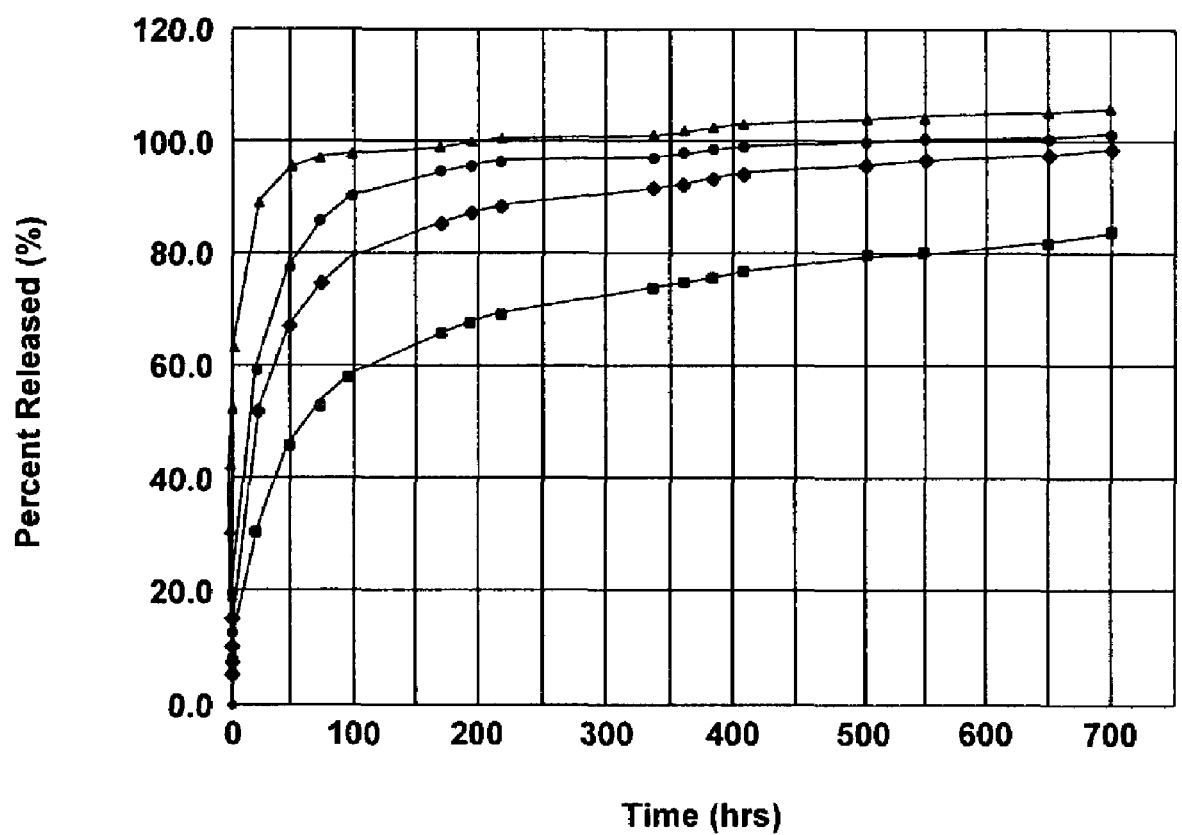
FIG. 12 is a plot of cumulative release of a drug from a drug-polymer stent, in accordance with one embodiment of the current invention.

FIG. 12 shows a plot of cumulative release of a drug from a drug-polymer stent, in accordance with one embodiment of the current invention at 1200. Given with a linear time scale, the plot shows the release kinetics of the antisense compound from the channel stents with various cap-coating polymers as described in FIG. 11. The plot shows the percent of drug released, with the majority of the drugs being released in the first two days, with reduced elution rates after the first couple of days, and significant portions of the drugs released after the first month.

Figure 13:
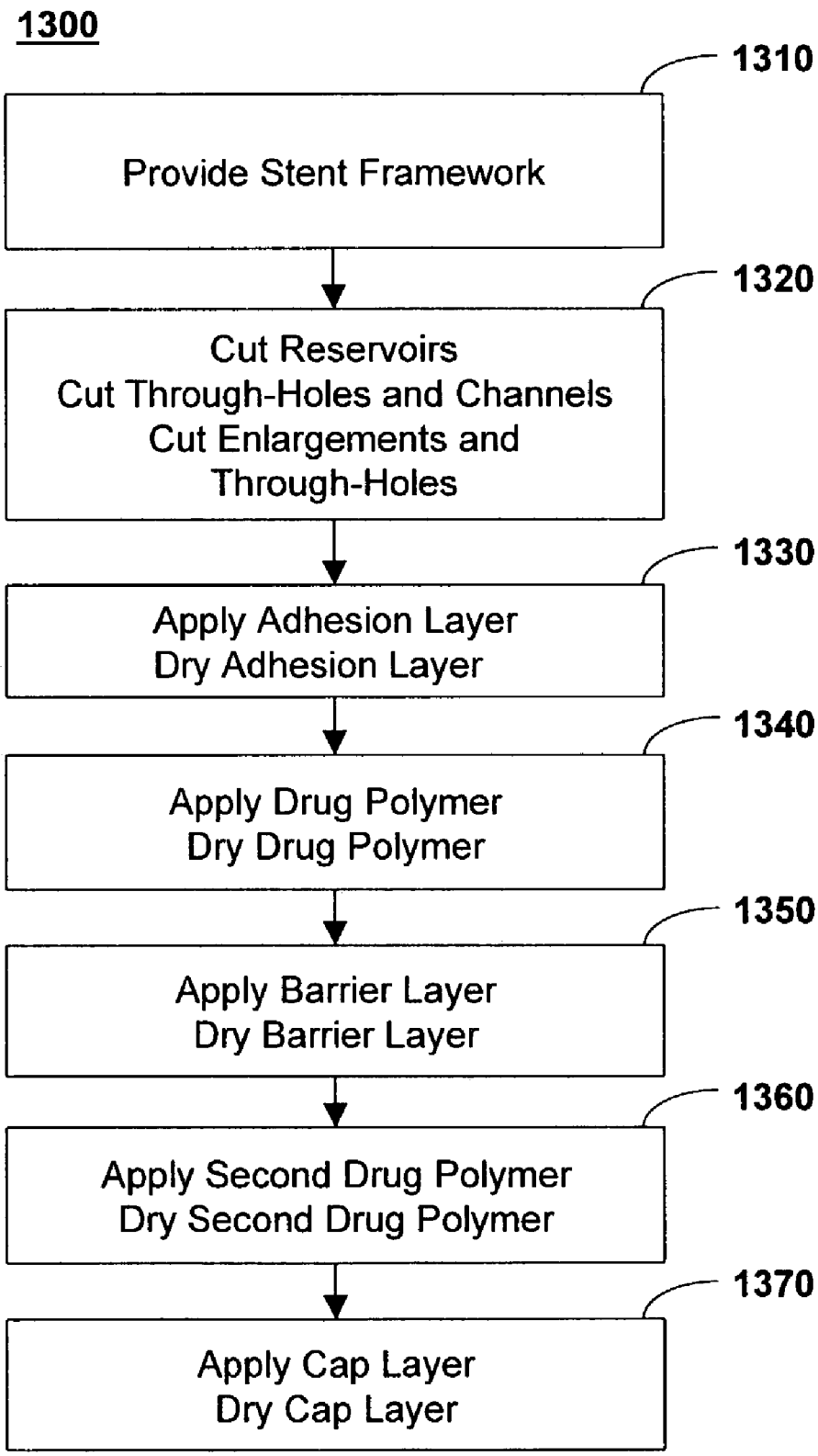
FIG. 13 is a flow diagram of a method for manufacturing a drug-polymer stent, in accordance with one embodiment of the current invention.

FIG. 13 shows a flow diagram of a method for manufacturing a drug-polymer stent, in accordance with one embodiment of the present invention at 1300. Method of manufacturing 1300 shows steps in making a drug-polymer stent with reservoirs and a drug polymer with a polymer layer. The polymer layer may be a barrier layer, a cap layer, or another drug polymer.

A stent framework is provided, as seen at block 1310. The stent framework may have a metallic or polymeric base. The stent framework may be formed by detailed cutting of a tube, by welding wires together, or by any suitable method for forming the stent framework.

A plurality of reservoirs is cut in the stent framework, as seen at block 1320. The plurality of reservoirs may be cut, for example, with a high-powered laser. The reservoirs may be etched, drilled or sawed into the stent framework. The reservoirs may comprise a plurality of through-holes, channels, or combinations thereof. The reservoirs may comprise a plurality of through-holes with an open region on the exterior or outer surface of the stent framework and an open region on the interior or inner surface of the stent framework. The holes may have anominally uniform diameter through the depth of the hole. The holes may be tapered, with a larger diameter at the exterior surface of the stent framework. The through-holes may be stepped, having a first diameter at the exterior surface of the stent framework and a second diameter at the interior surface of the stent framework, the first diameter being larger than the second diameter. The through-holes may have a smaller opening on the interior surface of the stent framework and a larger elongated opening on the exterior surface of the stent framework. Alternatively, the reservoirs may comprise channels along the exterior surface of the stent framework, or a combination of through-holes and channels. Enlargements may be formed in the vicinity of the through-holes to reduce stress when the stent is expanded. The enlargements may be formed, for example, when a high-powered laser is used to cut the stent framework from a thin-walled tube of metal or polymer.

An adhesion layer may be applied optionally to the stent framework to enhance the adhesion between subsequently applied drug polymers and the stent framework, as seen at block 1330. The adhesion layer may comprise, for example, a thin coating of a polyurethane, a phenoxy, poly(lactide-co-glycolide), polylactide, polysulfone, polycaprolactone, an adhesion promoter, or combinations thereof. The adhesion layer may be applied to at least one reservoir prior to the application of the drug polymer. The adhesion layer may be applied to the reservoirs and at least a portion of the stent framework. The adhesion layer may be applied by any suitable coating method such as spraying, dipping, painting, brushing or dispensing. A mask may be used when applying the adhesion coating. The adhesion layer may be dried at room temperature or at an elevated temperature suitable for driving off any solvents, and a nitrogen or vacuum environment may be used to assist the drying process.

A drug polymer is applied to reservoirs in the stent framework and possibly to a portion of the stent framework, as seen at block 1340. A drug-polymer solution including the drug polymer and a suitable solvent such as chloroform or tetrahydrofuran (THF) may be applied using any suitable application technique such as spraying, dipping, painting, brushing or dispensing. The drug may be sprayed into the reservoirs, for example, using an ultrasonic sprayer that creates a fine mist of the drug solution. A mask such as a tube with slits may be used to selectively position the drug polymer in the reservoirs. A tube may be positioned inside the stent to inhibit the application of the drug polymer to the interior surface of the stent framework. The drug polymer comprises a therapeutic compound. Examples of therapeutic compounds include an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, or combinations thereof. The drug-polymer solution is dried by driving off solvents in the solution using any suitable drying method such as baking at an elevated temperature in an inert ambient such as nitrogen or in vacuum. The drug-polymer solution may be dried by evaporating the solvent after application. The drying may be performed at room temperature and under ambient conditions. A nitrogen environment or other controlled environment may also be used. Alternatively, the drug-polymer solution can be dried by evaporating the majority of the solvent at room temperature, and further drying the solution in a vacuum environment between room temperature of about 25 degrees centigrade and 45 degrees centigrade or higher to extract any pockets of solvent buried within the drug-polymer coating. Additional coats may be added to thicken the drug coating or to increase the drug dosage, when needed. A polymer layer is applied to the dried drug polymer, the polymer layer comprising a barrier layer, a cap layer, or another drug polymer layer. The polymer layer may be applied to at least a portion of the interior surface of the exterior surface of the stent framework using a mask.

A barrier layer may optionally be applied and dried, as seen at block 1350. The barrier layer may be positioned on the first drug polymer to control the elution of drug from the underlying drug polymer. The barrier layer may comprise, for example, a silicone-urethane copolymer, a polyurethane, a phenoxy, ethylene vinyl acetate, polycaprolactone, poly (lactide-co-glycolide), polylactide, polysulfone, elastin, fibrin, collagen, chondroitin sulfate, a biocompatible polymer, a biostable polymer, a biodegradable polymer, or combinations thereof. The barrier layer may be applied using a suitable technique such as spraying, dipping, painting, brushing or dispensing.

A second drug polymer may be applied and dried, as seen at block 1360. The drug polymer may be applied using any suitable technique such as spraying, dipping, painting, brushing, or dispensing. A mask may be used to position the drug in the reservoirs and to reduce the drug polymer on the stent framework.

A third drug polymer may be applied if desired, such as for the case of controlled, phased delivery of two or more drugs from reservoirs formed in the stent framework.

A cap layer may optionally be applied and dried, as seen at block 1370. The cap layer may comprise, for example, a thin layer of a silicone-urethane copolymer, a polyurethane, a phenoxy, ethylene vinyl acetate, polycaprolactone, poly (lactide-co-glycolide), polylactide, polysulfone, elastin fibrin, collagen, chondroitin sulfate, a biocompatible polymer, a biostable polymer, a biodegradable polymer, or combinations thereof.

A cap layer may be optionally applied to the interior surface of the stent framework, the cap layer covering a drug polymer and controlling or inhibiting the elution of drug to the interior of the vessel when the stent is deployed. The cap layer may be applied to at least the interior surface of the stent framework by inserting the stent into a close-fitting tube prior to cap layer application.

In another embodiment of the invention, a stent including a plurality of channels formed therein may be fabricated and deployed for the release of an antisense compound into the vessel walls. The drug-polymer stent has a plurality of overlapping laser cut holes that are formed into a rectangular trough. Spraying may be used to deposit drugs into the reservoirs on the stent struts. The inside surface of the stent is masked with an aluminum tube and then mounted on a spray fixture of an ultrasonic sprayer. By masking the inside surface of the stent, the drug is deposited only into the reservoirs on the outer surface of the channel stent. A 1% solution of antisense drug in an 80/20 mixture of chloroform and methanol is sprayed onto the stent at a slow flow rate of about 0.05 ml/min to create a fine mist of the drug solution. A nitrogen-drying nozzle is placed at an angle parallel to the outer surface of the stent so that the nitrogen gas dries off the solvent and blows away drug particles on the struts but not the drug deposited inside the reservoirs. After the solvent has been allowed to evaporate and the true weight of drug determined, the stent is coated with either a biodegradable polymer such as polycaprolactone (PCL), polyglycolide (PGA) or poly(lactide-co-glycolide) (PLGA), or a biostable polymer such as a silicone-urethane copolymer, a polyurethane, or ethylene vinyl acetate (EVA). The outer polymer layer acts as a barrier for diffusion of drug from the reservoirs.

Various drugs or bioactive agents can be sprayed onto the channel stent during processing. For example, a small amount of an antiproliferative drug, on the order of 10–100 micrograms, can be sprayed onto the bottom of the channels and dried. Next, a thin layer of a selected polymer is sprayed over the antiproliferative drug to form a barrier layer. After drying to evaporate the solvent, an anti-inflammatory drug can be sprayed into the reservoirs in the same manner and then coated with a polymer of choice. The solvent in the second drug is chosen so that it does not significantly dissolve the first polymer barrier. An antisense compound or drug that can inhibit the expression of C-myc, a cellular homologue of avian myelocytomatosis virus oncogene, is then sprayed into the reservoirs and coated with a polymer of choice as a second cap layer. In this embodiment, the antisense compound, the anti-inflammatory drug and the anti-proliferative drug elute at different phases or timing during the restenosis process to combat C-myc expression in the earliest stage, inflammation during mid-stage, and proliferation/migration in a later stage.

FIG. 14 shows a flow diagram of a method for treating a vascular condition, in accordance with one embodiment of the present invention at 1400.

A drug-polymer stent with a stent framework and a plurality of reservoirs formed therein, a drug polymer positioned in the reservoirs, and a polymer layer positioned on the drug polymer is fabricated, as seen at block 1410.

The drug-polymer stent is positioned within a vessel of the body, as seen at block 1420. The drug-polymer stent may be positioned using a catheter and guidewire system, or any other suitable technique for positioning the stent at a predetermined location within the body.

The stent is expanded, as seen at block 1430. The stent may be deployed by applying pressure to a balloon used to expand the stent, or by retracting a sheath that allows the expansion of a self-expanding stent.

Once deployed, at least one drug is eluted from the drug polymer positioned in the reservoirs, as seen at block 1440. The drug is eluted in a controlled manner from at least the exterior of the stent framework. By using a combination of drug polymers, barrier layers and cap layers, multiple drugs may be delivered in a phased manner when the stent is deployed. Drugs may also be eluted from the interior surface of the stent framework, when the drug polymers are positioned in reservoirs having through-holes that extend to the inner surface of the stent.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A stent for delivering drugs to a vessel in a body comprising:
    a stent framework having a plurality of struts, each strut including a plurality of through-holes formed therein;
    a drug polymer positioned in the through-holes; and
    a polymer layer positioned on the drug polymer,
    wherein each of the plurality of struts comprises enlarged regions surrounding each of the plurality of through-holes and narrow regions positioned at least between each enlarged region, the enlarged regions having a first width greater than a second width of the narrow regions, and enlarged regions of one of the plurality of struts are aligned with enlarged regions of an adjacent one of the plurality of struts when the stent framework is in a compressed configuration.

2. The stent of claim 1 wherein the stent framework comprises one of a metallic base or a polymeric base.

3. The stent of claim 2 wherein the stent framework base comprises a material selected from the group consisting of stainless steel, nitinol, tantalum, MP35N alloy, platinum, titanium, a suitable biocompatible alloy, a suitable biocompatible polymer, and a combination thereof.

4. The stent of claim 1 wherein the through-holes have a first open region on an exterior surface of the stent framework and a second open region on an interior surface of the stent framework.

5. The stent of claim 4 wherein the through-holes have a nominally uniform diameter.

6. The stent of claim 4 wherein at least one through-hole is tapered, the tapered hole having a larger diameter at the exterior surface of the stent framework.

7. The stent of claim 4 wherein the through-holes have a first diameter at the exterior surface of the stent framework and a second diameter at the interior surface of the stent framework, the first diameter being larger than the second diameter.

8. The stent of claim 4 wherein the through-holes have a smaller opening on the interior surface of the stent framework and a larger elongated opening on the exterior surface of the stent framework.

9. The stent of claim 4 further comprising:
    a cap layer disposed on the interior surface of the stent framework, the cap layer covering at least a portion of the through-holes and providing a barrier characteristic to control an elution rate of a drug in the drug polymer from the interior surface of the stent framework.

10. The stent of claim 1 wherein the drug polymer comprises a therapeutic compound.

11. The stent of claim 10 wherein the therapeutic compound is selected from the group consisting of an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and a combination thereof.

12. The stent of claim 1 wherein the drug polymer comprises a first layer of a first drug polymer having a first pharmaceutical characteristic and the polymer layer comprises a second drug polymer having a second pharmaceutical characteristic.

13. The stent of claim 1 further comprising:
    a baffler layer positioned between the drug polymer and the polymer layer.

14. The stent of claim 13 wherein the baffler layer comprises a polymer selected from the group consisting of a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, and a combination thereof.

15. The stent of claim 1 wherein the drug polymer comprises a first drug-polymer layer including an anti-proliferative drug, a second drug-polymer layer including an anti-inflammatory drug, and a third drug-polymer layer including an antisense drug, the antisense drug, the anti-inflammatory drug and the anti-proliferative drug being eluted in a phased manner when the stent is deployed.

16. The stent of claim 1 wherein the polymer layer comprises a cap layer.

17. The stent of claim 16 wherein the cap layer is positioned on the drug polymer and at least a portion of an interior surface or an exterior surface of the stent framework.

18. The stent of claim 16 wherein the cap layer comprises a polymer selected from the group consisting of a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, and a combination thereof.

19. The stent of claim 1 further comprising:
    an adhesion layer positioned between the stent framework and the drug polymer.

20. The stent of claim 19 wherein the adhesion layer is selected from the group consisting of a polyurethane, a phenoxy, poly(lactide-co-glycolide), polylactide, polysulfone, polycaprolactone, an adhesion promoter, and a combination thereof.

21. The stent of claim 1 further comprising:
    a catheter coupled to the stent framework.

22. The stent of claim 21 wherein the catheter includes a balloon used to expand the stent.

23. The stent of claim 21 wherein the catheter includes a sheath that retracts to allow expansion of the stent.

* * * * *

UNITED STATES PATENT AND TRADEMARK OFFICE
CERTIFICATE OF CORRECTION

| | |
|---|---|
| PATENT NO. | : 7,163,555 B2 |
| APPLICATION NO. | : 10/408920 |
| DATED | : January 16, 2007 |
| INVENTOR(S) | : Thomas Q. Dinh |

It is certified that error appears in the above-identified patent and that said Letters Patent is hereby corrected as shown below:

Column 14, line 19, "a baffler layer positioned between the drug polymer and" should be changed to -- a barrier layer positioned between the drug polymer and --

Column 14, line 21, "14. The stent of claim13 wherein the baffler layer" should be changed to --14. The stent of claim 13 wherein the barrier layer--

Signed and Sealed this

Twenty-third Day of October, 2007

JON W. DUDAS
*Director of the United States Patent and Trademark Office*